(12) United States Patent
Robins

(10) Patent No.: US 8,231,839 B2
(45) Date of Patent: Jul. 31, 2012

(54) GAS DETECTION SYSTEM

(75) Inventor: Ian Robins, Dorset (GB)

(73) Assignee: Life Safety Distribution AG, Uster (CH)

( * ) Notice: Subject to any disclaimer, the term of this patent is extended or adjusted under 35 U.S.C. 154(b) by 482 days.

(21) Appl. No.: 11/658,959

(22) PCT Filed: Oct. 7, 2005

(86) PCT No.: PCT/GB2005/003877
§ 371 (c)(1),
(2), (4) Date: Jun. 12, 2009

(87) PCT Pub. No.: WO2006/038028
PCT Pub. Date: Apr. 13, 2006

(65) Prior Publication Data
US 2009/0301381 A1 Dec. 10, 2009

(30) Foreign Application Priority Data
Oct. 8, 2004 (EP) .................................... 04256223

(51) Int. Cl.
*G01N 33/00* (2006.01)
(52) U.S. Cl. ........ 422/401; 422/402; 422/420; 422/425; 422/68.1; 436/174; 436/178
(58) Field of Classification Search .................. 422/401, 422/402, 420, 425, 68.1; 436/174, 178
See application file for complete search history.

(56) References Cited

U.S. PATENT DOCUMENTS

| 3,723,064 A | 3/1973 | Liotta |
| 5,035,860 A * | 7/1991 | Kleingeld et al. ............ 422/413 |
| 5,464,588 A | 11/1995 | Bather et al. |
| 2004/0147036 A1 | 7/2004 | Krenn et al. |

FOREIGN PATENT DOCUMENTS

| EP | 0833158 B1 | 4/1998 |
| EP | 1037045 A2 | 9/2000 |

OTHER PUBLICATIONS

International Search Report dated Dec. 7, 2005 issued by ISA, European Patent Office, as published on Apr. 13, 2006 under International Publication No. WO 2006/038028 A1 by World Intellectual Property Organization, International Bureau.

* cited by examiner

*Primary Examiner* — Sam P Siefke
(74) *Attorney, Agent, or Firm* — Husch Blackwell

(57) ABSTRACT

The present invention provides a colorimetric gas detector comprising a substrate bearing a material that can react with a gas in an atmosphere being monitored and wherein the reaction causes the material to change the radiation at which the material absorbs or radiates radiation (the color-change material). The material is located in at least one discrete area of the substrate. By providing the color change material in discrete areas, the amount of such material can be reduced and different types of color-change material can be included on a common substrate to detect two or more gases simultaneously.

14 Claims, 1 Drawing Sheet

GAS DETECTION SYSTEM

TECHNICAL FIELD

The present invention relates to detectors, especially for detecting toxic gases, the detectors having a material that reacts with a gas or vapour (or a family of gases or vapours) being sensed (hereinafter referred to as a "target gas") and the reaction causes a change in the radiation absorption of the material, usually evidenced by a change in colour in the visible spectrum.

BACKGROUND ART

It is known to detect toxic gases using chemical cassettes having a paper tape impregnated with a specific chemical material; the paper is usually absorbent and is impregnated with the chemical material by dipping it into a trough of a solution of the material. The tape is subsequently dried and installed in a cassette. During use, the paper tape is placed in an analyser that draws gas from the atmosphere being monitored through the tape. The chemical material on the tape is chosen to react with the target gas and to change colour. The degree of colour change is a measure of the concentration of the target gas in the atmosphere being monitored. The analyser detects the change of colour and calculates the gas concentration by comparison to a table of known gas responses that has been pre-programmed into the analyser. The tape is advanced periodically to bring a fresh length of tape to the position within the analyser through which the target gas is drawn to expose a fresh length of tape to make a further measurement. One major advantage of the tape system is that a permanent visual record exists of positive gas responses as seen by the visible colour change of the tape.

The present system gives rise to several problems. Firstly, the material supported on the tape that changes radiation absorption properties on exposure to the target gas (hereinafter referred to as the "colour-change material") can give off a gas during reaction with the target gas. This evolved gas can lead to inaccuracies in the measurement.

Secondly, the tape and the colour-change material can degrade over time in response to temperature, humidity and/or light. It therefore has a limited shelf life and so only a limited stock can be held by the user.

It is critical that the tape is uniform along its length to ensure a uniform response to a given amount of target gas. Therefore, inconsistencies in the tape must be avoided. Also, if a paper tape includes variations in thickness, e.g. "lumps" within the paper material of the tape, this can cause the analyser to jam. Furthermore "lumps" in the tape can result in variable gas flow through the tape and therefore result in further inaccuracies in the measurement, ultimately possibly causing a false alarm or an alarm indicting that the detection system is not operating properly (fault alarm).

The colour-change material can be affected by gases in the atmosphere being monitored other than the target gases. Often, water vapour can change the response of the colour change materials to a target gas, leading to inaccuracies in the measurement.

It is an object of the present invention to overcome or alleviate some or all of the above problems and/or to provide a system bearing colour-change materials that can be used to detect two or more gases.

DISCLOSURE OF INVENTION

According to the present invention, there is provided a colorimetric gas detector comprising a substrate bearing a material that can react with a target gas to produce a change in the radiation absorbed by the material, wherein the material is located in one or more, preferably two or more, discrete areas of the substrate.

The limitation of the material to discrete areas on the substrate has the advantage that less colour-change material is required. In addition, it allows the sheet to perform additional functions that the prior art could not, as discussed below.

According to a first embodiment, the colour-change material used in one discrete area of the substrate differs from that used in one or more other areas. For example, in one area, the colour-change material could be present in a different amount or dose as compared to that at another area. This allows a wider range of concentration of gases to be detected. Using such an arrangement, if a high concentration of the target gas is present in the atmosphere being monitored, then all the material in the low dose area of the colour-change material would change its colour and it would not be possible to discriminate between various levels of concentration of the target gas; on the other hand, in a high dose area, only a portion of the colour-change material would change colour and accordingly could give an indication of the concentration of the target gas. Conversely, if the target gas is present at low concentration, then the area containing a low dose of colour-change material would give a better indication of the concentration of gas than would be the case in the high dose area. Accordingly, by using two or more discrete areas with different amounts or doses of colour-change material, it is possible to measure both high concentrations and low concentrations of target gas.

Alternatively, different colour-change materials could be provided in the different discrete areas so that two or more target gases can be detected simultaneously. Such an arrangement can also be used to eliminate the effects of, or at least alert an operator to the presence of, a cross inference gas, as will now be described.

If the colour-change material not only reacts with the target gas but also with one or more other gases that might be present in the atmosphere being monitored, it is possible to provide, in a first area, a colour-change material that reacts with both the target gas and with the cross-reacting gas, while providing, in a second area, a second colour-change material that reacts only with the cross-reacting gas. In these circumstances, the concentration of the cross-reacting gas can be obtained from the second area and subtracted from the colour-change that has been measured in the first area, thereby giving an indication of the concentration of the target gas.

Preferably, the different discrete areas are grouped together so that they can be read simultaneously by an appropriate number of light sensitive elements. Thus, the first area may be a semi-circle and a second area forming an adjacent semi-circle so that, together, they complete a full circle. Alternatively, the various areas may be formed as stripes located in sequence across the substrate.

The substrate may be a strip or tape, which may be housed in a cassette, so that sequential areas of the strip or tape are exposed to the atmosphere being monitored in the same arrangement as is currently used, as described above. In this case, the substrate could be gas porous to allow a sample of the gas from the monitored area to be drawn through or past the substrate. In addition, the substrate is preferably liquid-absorbent so that the liquid absorbent material is readily held by the substrate. However, it should not be so absorbent that deposited areas of the colour-change material migrate from the intended discrete areas; this is especially important when two or more areas are located adjacent to each other.

If the degree of colour-change in the colour-change material is being used to give an indication of the amount of target gas in the atmosphere being monitored, then it is important that a consistent dose of colour-change material should be deposited or alternatively that the system should be capable of calibration. The amount of colour-change material deposited in any discrete area could be measured directly, e.g. colorimetrically if the colour-change material is itself coloured. However, if it is not coloured, then a colour marker may be included in the ink that is deposited to give a measure of the amount of colour-change material in any discrete area.

Such an arrangement also provides a visible indication that the colour-change material is being deposited, especially if the deposited material is otherwise colourless, when deposited.

The present invention also relates to a method of making a colorimetric gas detector as defined above wherein the colour-change material is deposited in the individual discrete areas, e.g. by at least one inkjet. Also other printing techniques such as tamper printing, offset litho printing, etc. can be used. An advantage of using inkjet printing is that the colour-change material may be applied to the substrate with a relatively low capital investment allowing the users to prepare their own detectors (i.e. substrate bearing colour-changing material), thereby overcoming the problem of having to order them from a supplier on a frequent basis because of their short shelf-life.

According to a third aspect of the present invention, there is provided a method of detecting a gas in an atmosphere being monitored, which comprises bringing a sample from the atmosphere into contact with one or more discrete areas of a colorimetric gas detector as defined above, for example by drawing the sample gas through or past the substrate.

DETAILED DESCRIPTION OF INVENTION

Figure 1:
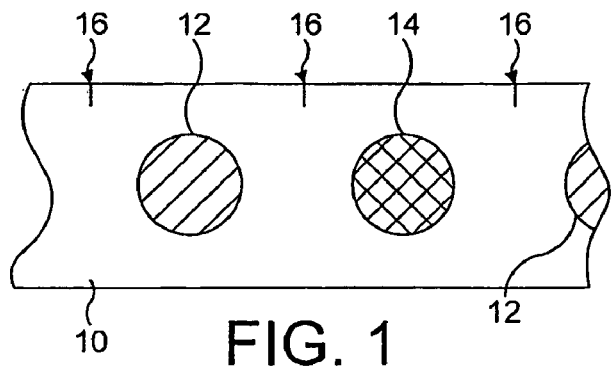
FIGS. 1 to 4 show alternative forms of sheet or tape for use in a colorimetric gas sensing apparatus.

Referring initially to FIG. 1, there is shown a tape made up of a substrate 10 on which is deposited a row of dots 12, 14; alternate dots are formed by different colour-change materials so, for example, dot 12 may be made up of one type of colour-change material and dot 14 may be formed from another type of colour-change material, shown by the different cross-hatching in the dots. The dots are deposited by inkjet printing techniques.

As with existing colorimetric gas detection, gas from an atmosphere being monitored may be drawn sequentially through or past dots 12, 14 or may be drawn simultaneously through or past adjacent pairs of dots 12, 14.

The dots 12, 14 are deposited from inkjets using known piezoelectric print jet heads.

Examples of materials that can be used in the formulations of the deposits are any of those known from the prior art to be suitable for bringing about a colour change and three examples are:

Material 1

A solution in water or an organic solvent such as methanol that contains:
  0.1 weight percent of eosine yellowish (colour index: acid red 87) which is a fluoscine based dye,
  0.3 weight percent of para-toluenesulphonic acid, and
  15 weight percent polyhydric alcohol such as glycerin, This material when dried is substantially transparent or very pale pink in colour because the pH of the material is maintained very low due to the acid (the dye only shows its colour when neutral or basic). This material can be used to detect the concentration of a basic gaseous component (such as ammonia) by the gas making the material more basic and therefore the natural colour of the dye can emerge. Colour change—clear to yellow Material 2

Same as Material 1 except that the eosine yellowish is replaced by rose benzal, phloxine, eosine bluish, or erythrosine. The para-toluenesulphonic acid may be replaced by naphthalenesulphonic acid or benzensulphonic acid. Material 2 is also used for the detection of basic gases.

Material 3

Solvent: 1.5 ml. cone. nitric acid;
  25 ml. glycerol; and
  224 ml. methanol.

Active ingredient: 2.5 grams silver nitrate

Substrate: a paper tape coated with silicic acid (or silica gel)

This material can be used for detecting metal hydrides such as arsine, phosphine, diborane. On exposure to these materials, the deposited material undergoes a colour change from clear to grey/black.

Instead of conc. nitric acid, other organic or inorganic acids may be used, e.g. one of the acids mentioned in Materials 1 and 2 as previously described in Materials 1 and 2. An alcohol (methanol) was selected as the solvent because it allows the tape to dry readily when processed relative to a water-based solution but other alcohols and solvents may be used, e.g. ethyl alcohol and isopropyl alcohol, although volatile solvents are preferred. The glycerol increases the adsorbent ability of the tape by keeping the tape moist enough to allow the intended reaction between incoming hydride gas and the tape reagents to occur; other glycols can be used, e.g. ethylene glycol, propylene glycol and trimethylene glycol. The use of methanol and glycerol, however, is preferred on the grounds of cost.

A tape on which the above Material 3 is deposited maintains a white background for at least six months under normal storage conditions at room temperature with protection from light. Even after six months, the tape can still displays sensitivity ($\pm 10\%$) to hydride gases.

A more generalised solvent for the silver nitrate active ingredient is
  0.1-5% acid;
  5-20% glycol; and
  94.9-75% alcohol.

For example, dot 12 may be a deposit of Material 1 and dot 14 may be a deposit of material 3. With this arrangement, it is possible to detect both a basic gas and a hydride in a single atmosphere.

Once a sample gas from the atmosphere being monitored has been drawn through or past dots 12, 14, they are sequentially or simultaneously exposed to a source of visible radiation, which may simply be ambient radiation, and the radiation transmitted by the dots 12, 14 passes to a detector, which measures the change in colour according to a pre-programmed look-up table. Since the degree of colour-change will depend on the concentration of gas within the atmosphere, the change of colour is an indication of the concentration of the target gas.

As stated above, the dots 12, 14 are optically analysed. Index markings 16 may be provided on the tape to ensure correct alignment of the dots with the optical radiation source and the detector.

Dots 12 and 14, instead of being made from different chemical entities, may be made of the same entity but in different doses. In this way, as described above, it is possible to measure a wider range of concentrations of target gas.

As discussed above, the known method of making colour-change tape involves weaving the substrate tape through coating troughs containing a bath of colour-change material to impregnate the whole of the tape with the colour-change material; the tape is then dried over an extended period. In this way, the whole of the tape is impregnated by colour-change material. Not only does the arrangement of the present invention save colour-change material, since a lesser amount of colour-change material is used, it also saves drying the whole tape and, furthermore, provides a smaller area of colour-change material which can give off gas in use (this "off gas" can interfere with the measurement of target gas). In addition, the reduced drying time due to ink-jet deposition and more precise dosing of the colour-change material on the substrate allows the tape of the present invention to be manufactured much more quickly than the prior art tape.

In another embodiment, the dot 12 could be sensitive to a target gas and to a cross-interfering gas, e.g. carbon monoxide and water vapour respectively. Dot 14 could then be made of a material that is sensitive only to water vapour so that the amount of water vapour in the atmosphere can be measured using dot 14 and the effect of the water vapour subtracted from the combined measurement of carbon monoxide and water vapour by dot 12 to give an overall concentration of carbon monoxide. Instead of providing two separate dots 12, 14, single dots 18 (see FIG. 2) could be provided. Each dot 18 is made up of two semi-circles 20, 22, containing, respectively, the colour-change material used in dots 12, 14, as described above. The advantage of the arrangement in FIG. 2 is that both colour-change materials in semi-circle 20, 22 can be simultaneously exposed to gas from the atmosphere being monitored and can simultaneously be tested for colour-change, preferably using separate light-sensitive sensors for detecting the radiation transmitted from each semi-circle.

Of course, instead of providing semi-circles of two different colour-change materials, three or four different colour-change materials could be used, in which case the dots must be divided up into three or four segments. The dots may be of any shape, e.g. round or square, and may be any size.

Figure 2:
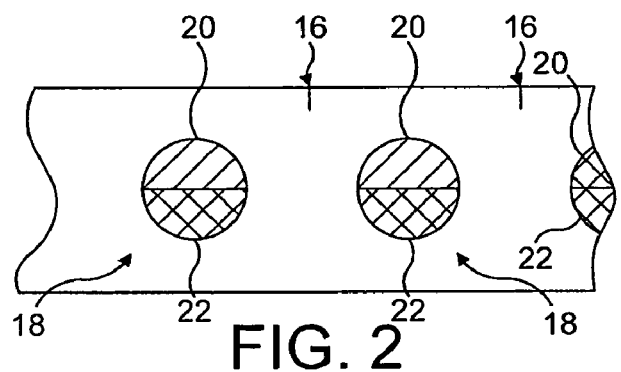
Figure 3:
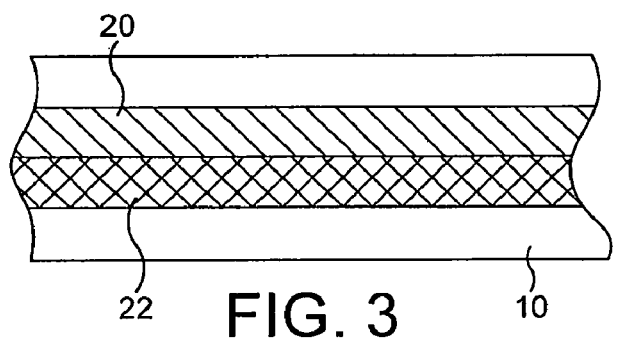

The arrangement shown in FIG. 3 is the same as that shown in FIG. 2 but instead of having semi-circles, two stripes of the different colour-change material are used. Such an arrangement has the advantage over FIGS. 1 and 2 that there is no need to provide index markings 16 to align the colour-change material with gas inlets for allowing sample gas from the atmosphere being monitored to contact the colour-change material or to align the dots with the radiation source/sensor.

Figure 4:
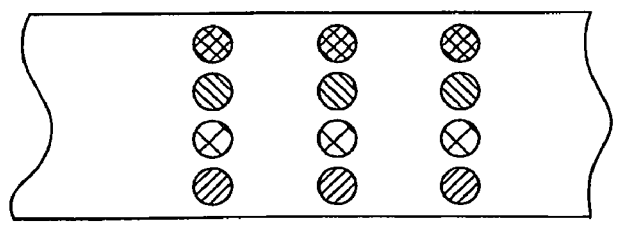

The arrangement shown in FIG. 4 uses rows of four dots arranged transverse to the axis of the tape. Each dot uses a different colour-change material and/or a different concentration of the same colour-change material so as to provide for detection of a wide range of concentrations of multiple gases and, possibly, also to allow for interferences from cross-sensitive gases or water vapour to be measured. Instead of measuring the precise colour-change, it is possible, by providing a suitable pattern of individual areas, that the concentration and nature of the gas can be discovered by pattern recognition.

The radiation transmitted by the individual areas may be detected by a photosensitive cell having suitable filters to restrict the radiation reaching the cell to those transmitted when the colour-change material has reacted with the target gas. This can be achieved through the use of a still or video camera by forming an image of the areas of colour change material either in colour or in a greyscale and analysing the pixels forming the image of the areas to detect and optionally also record the colour change.

Inkjet printers are relatively cheap and accordingly, instead of making cassettes containing paper tapes in a factory and shipping them to customers, the customers can prepare their own tapes. This means that the amount of stock that needs to be carried can be reduced and the tapes will not degrade through over-long storage. The colour change materials can then be supplied in replaceable inkjet cartridges.

Alternatively, one or more inkjet printing heads may be incorporated into the gas detection equipment so that the colour-change materials are deposited and dried immediately before being exposed to the atmosphere being monitored.

A third possibility is not to dry the tape before exposing it to the atmosphere being monitored and so the colour-change material will be wet; however, this requires either a relatively short time between deposit of the colour-change material and the exposure to the atmosphere being monitored or a carefully-controlled atmosphere being maintained between the deposition and the exposure to the atmosphere being monitored. Obviously, such an arrangement cannot be used where the colour-change material is sensitive to moisture.

If the colour-change material is deposited in situ shortly before a reading takes place, then it is possible to tailor the amount of colour-change material deposited to provide the optimum response for the concentrations of target gas previously detected. In this way, the system "learns" the most likely concentrations of target gas it is to encounter and adjusts the dose of colour-change material deposited to provide appropriate sensitivity. Alternatively, a consistent dose of colour-change material may be deposited but the time that the colour-change material is exposed to the atmosphere being monitored could be adjusted to provide the optimum sensitivity to the "learnt" concentrations of target gas, as assessed by previous readings of target gas concentrations.

Although the above description has been specifically described in relation to tape, it is not necessary that the substrate containing the discrete areas of colour-change material should be a tape and other formats can be used, for example an A4 sheet of paper.

In one embodiment, the plural discrete areas of the substrate that include colour-change material and that are contacted at the same time with the atmosphere being monitored are exposed to the same atmosphere rather than being isolated from each other and exposed to individual samples of the atmosphere.

The invention claimed is:

1. A colorimetric gas detector comprising a substrate, the substrate bearing a dry, self-contained color change material that can react with a target gas in an atmosphere being monitored wherein the reaction causes the material to alter a parameter indicative of one of absorption or radiation by the material, wherein color-change material is located on at least two discrete areas, and wherein a concentration of the color-change material in one discrete area is different from a concentration of the color-change material in a second discrete area, the first and the second areas being adjacent to each other on the substrate, wherein the color-change material is deposited on the substrate by printing and wherein the discrete areas are arranged in a repeating pattern on the substrate that allows periodic advancement of the substrate to bring a fresh length of the substrate with a fresh at least two discrete areas into a position so that sequential areas of the substrate are exposed to the target gas to make further measurements.

2. A colorimetric gas detector comprising a substrate, the substrate bearing dry, self contained color change materials that can react with a target gas in an atmosphere being monitored, wherein the reaction causes the materials to alter a parameter indicative of one of absorption or radiation by the material, wherein color-change material is located on at least two discrete areas, wherein a first color-change material is provided at the one discrete area and a second, different, color-change material is provided at the second area, the first and second areas being adjacent to each other on the substrate, wherein the color-change material is deposited on the substrate by printing and wherein the discrete areas are arranged in a repeating pattern on the substrate that allows periodic advancement of the substrate to bring a fresh length of the substrate with a fresh at least two discrete areas into a position so that sequential areas of the substrate are exposed to the target gas to make further measurements.

3. A colorimetric gas detector as claimed in claim 2, wherein the first color-change material is altered by one of, a reaction with the target gas and a second, cross-interfering gas or where the presence of the second, cross-interfering gas affects the reaction of the first color-change material with the target gas, and, wherein the second color-change material can react with the second cross-interfering gas but not the target gas.

4. A colorimetric gas detector as in claim 1, where first and second areas are formed as stripes.

5. A colorimetric gas detector as in claim 1 which includes indexing markings carried by the substrate for defining the positions of at least one discrete area relative to the markings.

6. A colorimetric gas detector as in claim 1 wherein the substrate is formed as at least one of a sheet, strip, or tape, and is at least one of gas-porous or liquid-absorbent.

7. A method of detecting a target gas in an atmosphere being monitored comprising providing a common substrate;

providing a plurality of spaced apart regions, on the substrate, each of which carry a target gas responsive, color changing material;

bringing a sample from the atmosphere into contact with at least one of the regions by one of drawing the sample through or past the region;

measuring at least one of radiation transmittance or radiation reflection from the material;

comparing measured radiation with a reference and deriving therefrom a measure of the concentration of the target gas, wherein providing a plurality of spaced apart regions includes printing the target gas responsive, color change material on the spaced apart regions of the substrate; and advancing the common substrate to bring a fresh length of the common substrate and target gas responsive, color changing materials into a position for drawing a sample from the atmosphere through or past one of the spaced apart regions of the fresh length and for further measuring of the least one of radiation transmittance or radiation reflection from the material.

8. A method as in claim 7 where providing includes providing first and second, adjacent regions, on the substrate, carrying first and second different gas responsive materials.

9. A method as in claim 8 where measuring includes measuring radiation associated with adjacent regions substantially at the same time.

10. A method as in claim 8 where drawing the sample includes drawing the sample through or past adjacent, regions substantially at the same time.

11. A method as in claim 7 where providing a common substrate includes providing an elongated common substrate.

12. A method as in claim 11 including spacing at least some of the regions axially along the elongated substrate.

13. A method as in claim 12 including spacing at least some of the regions laterally along the substrate.

14. A detector as in claim 2 wherein the regions abut one another.

* * * * *